United States Patent [19]

Christensen et al.

[11] Patent Number: 5,053,185
[45] Date of Patent: Oct. 1, 1991

[54] MATERIAL ANALYZER WITH CAROUSEL

[75] Inventors: Scott C. Christensen, Sioux Falls, S. Dak.; Raymond J. Proctor, San Diego; Richard L., Conwell, Del Mar, both of Calif.

[73] Assignee: Gamma-Metrics, San Diego, Calif.

[21] Appl. No.: 527,483

[22] Filed: May 23, 1990

[51] Int. Cl.$^5$ .............................................. G21G 1/121
[52] U.S. Cl. ..................................... 376/157; 376/158
[58] Field of Search ................ 376/157, 158; 222/145; 366/220

[56] References Cited

U.S. PATENT DOCUMENTS

| | | | |
|---|---|---|---|
| 2,514,126 | 7/1950 | Fischer | 366/220 |
| 4,117,935 | 10/1978 | Richardson et al. | 209/586 |
| 4,147,618 | 4/1979 | Richardson et al. | 209/589 |
| 4,283,148 | 8/1981 | Peterson | 366/142 |
| 4,459,258 | 7/1984 | Zeits et al. | 376/157 |
| 4,496,070 | 1/1985 | Lane, Jr. | 220/306 |
| 4,582,992 | 4/1986 | Atwell et al. | 250/359.1 |

Primary Examiner—Donald P. Walsh
Assistant Examiner—Meena Chelliah
Attorney, Agent, or Firm—Edward W. Callan

[57] ABSTRACT

A material analyzer includes a container; a radiation source disposed within the container; a detector disposed within the container for detecting radiation that is secondarily emitted by a material sample within an activation region located between the radiation source and the detector when the material sample is bombarded by radiation from the radiation source and for producing signals in response to said secondarily emitted radiation; a computer for processing the signals to determine the content of the material sample; and a carousel for transporting a material sample from outside the container to within the activation region. The carousel is disposed about an axis of rotation located between the activation region and a receiving region located outside the container, and has a pair of sample containment chambers that are alternately moved between the receiving region and the activation region when the carousel is rotated about said axis. Material samples are placed in buckets for loading into the sample containment chambers. The bucket includes a perimetric side wall having a predominant surface area that is contoured on opposite sides of the side wall to define exterior indentations in the predominant surface area; and a handle, including a pair of tongs shaped and disposed for insertion into the side wall indentations, and a telescopic handle joining the tongs. A radiation shield within the container shields the outside of the container from radiation derived in the activation region from the radiation source.

10 Claims, 4 Drawing Sheets

MATERIAL ANALYZER WITH CAROUSEL

BACKGROUND OF THE INVENTION

The present invention generally pertains to material analyzers and is particularly directed to transporting materials samples to an activation region of the material analyzer for analysis.

Material analers are used to determine and measure the content of material samples. Prior art material analyzers are described in U.S. Pat. No. 4,582,992 to Thomas L. Atwell, James F. Miller, Ernesto Corte, Richard L. Conwell and Clinton L. Lingren and the publications cited therein.

In a typical prior art material analyzer, a material sample is positioned within an activation region located between a radiation source and a detector disposed for detecting radiation that is secondarily emitted by a material sample within the activation region when the material sample is bombarded by radiation from the radiation source. The detector produces signals in response to the secondarily emitted radiation; and a computer processing the signals to determine the content of the material sample. The radiation source and the detector are disposed within a container and are shielded by radiation shielding material within the container in order to shield the outside of the container from radiation derived from the radiation source.

In a prior art material analyzer designed to analyze bucket-size samples of material, the material sample is transported into the activation region from outside the container by use of a drawer that includes a sample containment chamber. The drawer is slid out from the container; the material sample is placed in the sample containment chamber; and the drawer is slid into the container to position the material sample within the activation region. After the material sample has been analyzed, the drawer is slid out from the container and the material sample is removed from the sample containment chamber.

SUMMARY OF THE INVENTION

The material analyzer of the present invention is an apparatus that includes a container; a radiation source disposed within the container; a detector disposed within the container for detecting radiation that is secondarily emitted by a material sample within an activation region located between the radiation source and the detector when the material sample is bombarded by radiation from the radiation source and for producing signals in response to said secondarily emitted radiation; a radiation shield within the container for shielding the outside of the container from radiation derived in the activation region from the radiation source; means for processing said signals to determine the content of the material sample; and means for transporting a material sample from outside the container to within said activation region; wherein the transporting means comprise a carousel, disposed about an axis of rotation located between the activation region and a receiving region located outside the container, and having at least one sample containment chamber that is moved between the receiving region and the activation region when the carousel is rotated about said axis.

By using a carousel instead of a drawer to transport the material sample from outside the container to within the activation region, the apparatus of the present invention requires less space when being used, and thereby enables the use of the apparatus in a relatively small space such as the cargo compartment of a vehicle used to transport the material analyzer to a site where samples of the sampled material are being mined or otherwise produced.

Another advantage of the use of a carousel is that the carousel may further include a second sample containment chamber located on the opposite side of the carousel from the first mentioned containment chamber; so that as one material sample within one sample containment chamber is disposed within the activation region and being analyzed, the previous material sample is removed from the second sample containment chamber and the next material sample is placed within the second sample containment chamber, thereby significantly increasing the rate at which samples can be analyzed. Also, by providing oppositely disposed sample containment chambers in the carousel, no significant change occurs in the center of gravity of the carousel as the sample is transported from outside the container to within the activation region. This obviates the need to provide counterweights, as may be required when a drawer is used.

In an embodiment in which the radiation source is disposed below the sample containment chamber when the sample containment chamber is in the activation region, and the detector is disposed above the sample containment chamber when the sample containment chamber is in the activation region; the carousel further includes a radiation shield disposed laterally around the sample containment chamber in order to prevent the material sample and/or the detector from being bombarded by secondarily emitted radiation from materials within the carousel that are disposed at the sides of the sample containment chamber.

In another aspect, the present invention further provides a removable bucket dimensioned for placement within the sample containment chamber. The bucket includes a perimetric side wall having a predominant surface area that is contoured on opposite sides of the side wall to contain exterior indentations in said predominant surface area; and a handle, including a pair of tongs shaped and disposed for insertion into the side wall indentations, and telescopic handle joining the tongs so that the tongs can be moved toward each other to fit within the side wall indentations in order to grip the bucket and thereby enable the bucket to be transported by using the handle, and so that the tongs can be moved away from each other to enable the handle to be removed from the bucket after the bucket has been so transported.

In a further aspect, the present invention also provides a sample mixer. The sample mixer includes a Y-shaped container having a hollow leg and two hollow arms that open into the leg, wherein each arm has an extended end that is closed, and wherein the leg has an extended end that is open and dimensioned to fit precisely against a rim at an open end of the bucket; a shutter attached to the extended end of the leg for movement between open and closed positions in order to prevent sample material from flowing out of the container from the extended end of the leg when the shutter is in the closed position and for enabling sample material to flow into or from the container through the extended end of the leg when the shutter is in the open position; and an axle, with the container being disposed on the axle for rotation about an axis that is normal to the leg so that sample material within the container can be mixed by rotating the container about the axle when the shutter is in the closed position.

Additional features of the present invention are described in relation to the description of the preferred embodiment.

DESCRIPTION OF THE PREFERRED EMBODIMENT

Figure 1:
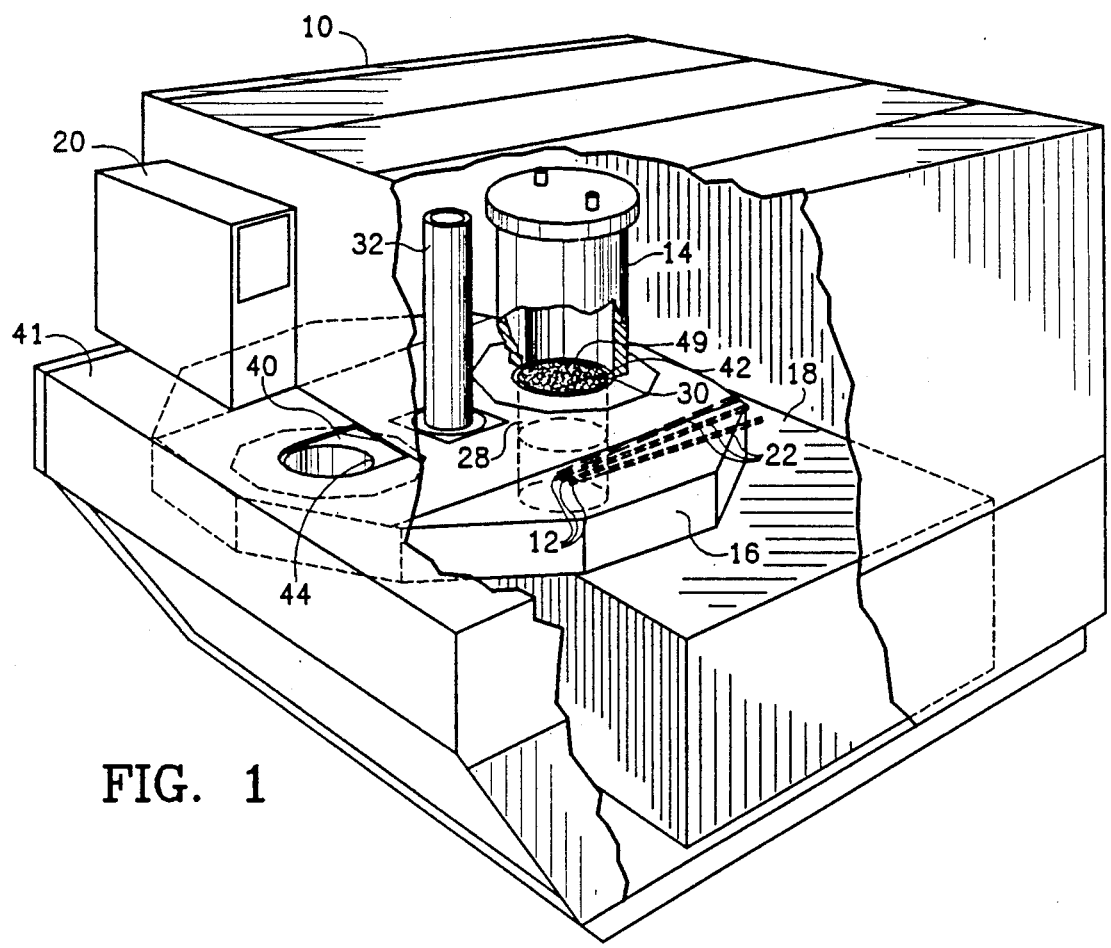
FIG. 1 is a perspective view of the material analyzer of the present invention with portions cut away to better show the relative placement of the carousel, the radiation source and the detector.
Figure 2:
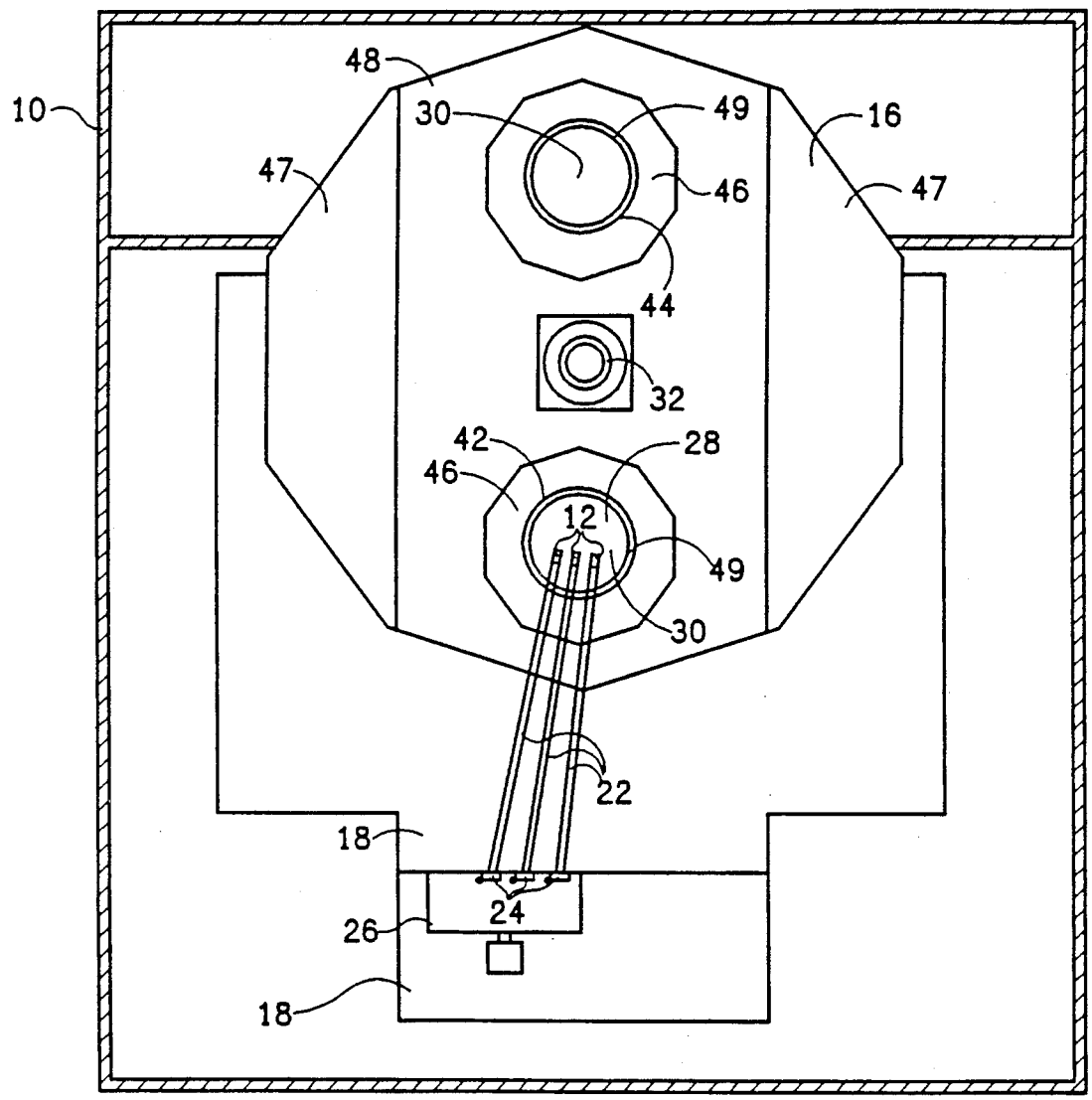
FIG. 2 is a top view of the material analyzer of FIG. 1 taken along a horizontal plane immediately above the carousel.

In a preferred embodiment of the present invention, as shown in FIGS. 1, 2, 3 and 4, the material analyzer includes a container 10, a radiation source 12, a detector 14, a carousel 16, radiation shielding material 18 and a computer 20. The radiation source 12, the detector 14, the carousel 16 and the radiation shielding material 18 are disposed at least partially within the container 10.

The radiation source 12 includes neutron soruces 12 secured to the ends of three rods 22, which are fastened to brackets 24 attached to an exterior wall of the container 10. The rods 22 are not radioactive. The brackets 24 are covered by a locked cover 26 that may be unlocked and removed when the rods 22 and the neutron sources 12 secured thereto are removed from or inserted within the container 10.

The detector 14 is disposed above the radiation source 12. An activation region 28 is located between the radiation source 12 and the detector 14. The detector 14 is disposed for detecting radiation that is secondarily emitted by a material sample 30 within the activation region 28 when the material sample 30 is bombarded by radiation from the radiation source 12. The detector 14 produces signals in response to said secondarily emitted radiation; and the computer 20 processes said signals to determine the content of the material sample 30. The results of said processing by the computer 20 are displayed by a monitor (not shown) and printed by a printer (not shown).

The radiation shielding material 18 is disposed within the container 10 for shielding the outside of the container 10 from radiation derived from the radiation source 12, including both direct radiation from the radiation source 12 and secondarily emitted radiation derived in the activation region 28 from the material sample 30.

Figure 3:
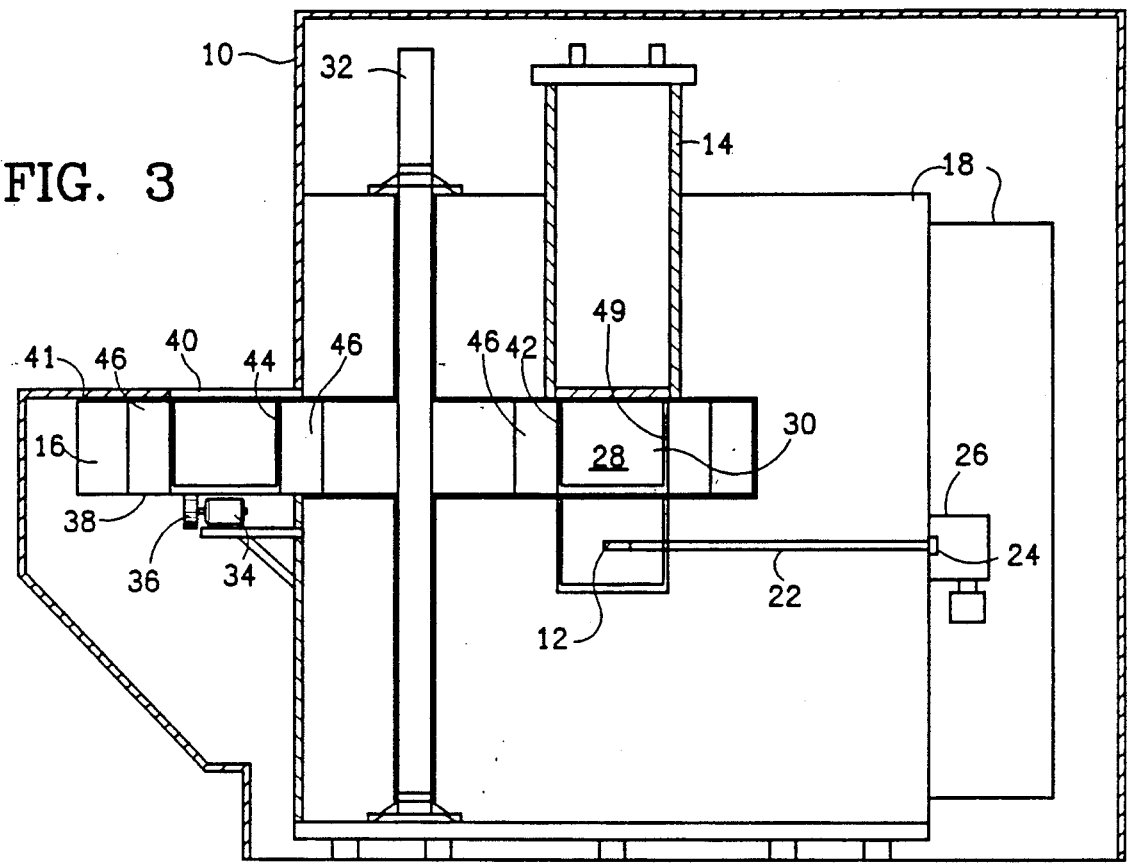
FIG. 3 is a side view of the material analyzer of FIG. 1 taken along a vertical plane adjacent the activation region.

The carousel 16 is disposed for rotation about an axle 32. The carousel 16 is rotated by a motor 34 and a rubber wheel 36 mounted on the shaft of the motor 34 (as shown in FIG. 3), with the motor 34 and rubber wheel 36 being located beneath the carousel 16 so that the rubber wheel 36 continuously contacts an under surface 38 of the carousel 16. The axle 32 defines an axis of rotation which is located between the activation region 28 and a receiving region 40 located outside the container 10.

In alternative embodiments (not shown), the carousel is mounted on the carousel 16 to the axle 32 and rotated by driving the axle; or is rotated by driving the perimeter of the carousel 16.

The carousel 16 includes two sample containment chambers 42, 44 located on opposite sides of the carousel 16 such that the carousel 16 can be rotated to position one sample containment chamber 42 within the activation region 28 and at the same time position the other sample containment chamber 44 within the receiving region 40 outside the container 10.

The carousel 16 also includes a radiation shield 46 disposed laterally around each sample containment chamber 42, 44 in order to prevent the material sample 30 and/or the detector 14 from being bombarded by secondarily emitted radiation from materials within the carousel 16 that are disposed at the sides of the sample containment chambers 42, 44.

The width of the carousel 16 is approximately four feet (1.2 m), which is considerably more than the width of a typical doorway, which is about thirty inches (75 cm). Therefore, in order to enable the carousel 16, which is quite heavy, to be moved through a doorway without having to be severely tipped from a horizontal orientation, outside portions 47 of the carousel 16 on two opposite sides of the carousel 16 that do not contain the sample containment chambers 42, 44 are readily removable from a center portion 48 of the carousel that does not exceed thirty inches in width. See FIG. 2.

When the sampled material is fluid material, such as granular material, the material sample 30 is placed in a bucket 49, which is placed in one of the sample containment chambers 42, 44. Typically a plurality of buckets 49 are loaded with material samples 30 prior to beginning analysis of a series of samples. Typically the buckets 49 are quite heavy and need to be lifted with a handle 50 to lessen the chance of the material sample 30 being spilled during handling of the bucket 49. Providing the buckets with handles also allows one person to carry two buckets simultaneously.

Figure 5:
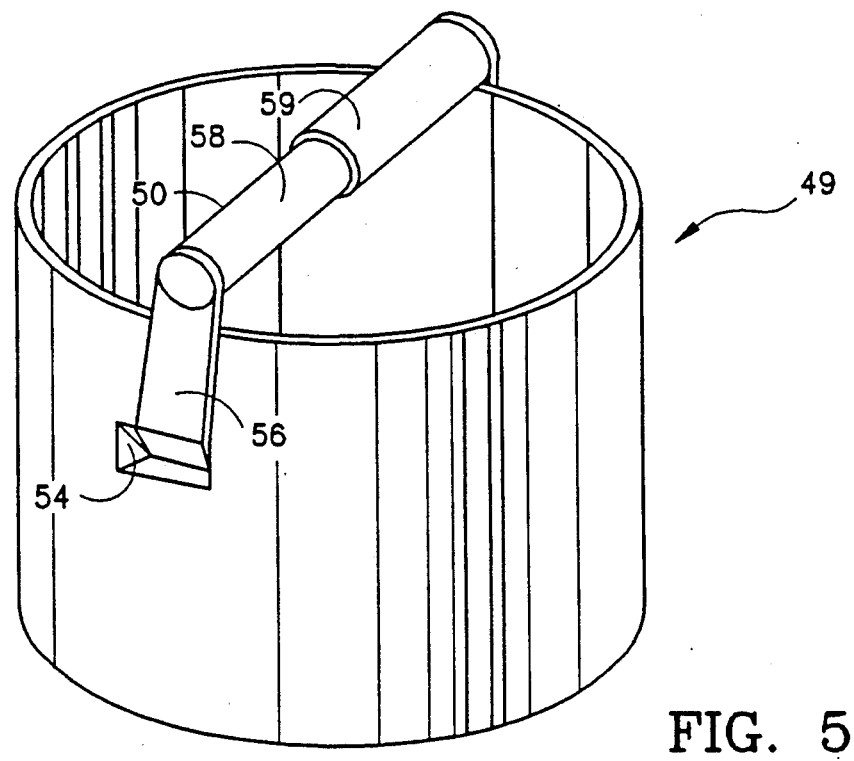
FIG. 5 is a perspective view of a sample bucket used with the material analyzer of FIG. 1.

Referring to FIG. 5, each bucket 49 includes a perimetric side wall 52 having a predominant surface area that is contoured on opposite sides of the side wall to contain exterior indentations 54 in said predominant surface area. In the preferred emboidment, the bucket 49 is made of plastic material. When the bucket 49 is placed in the sample containment chamber 42, 44, the bucket 49 does not extend beyond the sample containment chamber; and the predominant side wall area of the bucket fits closely within the sample containment chamber. The handle 50 includes a pair of tongs 56 that aare shaped and disposed for insertion into the side wall indentations 54. The handle 50 includes two telescopic sections 58, 59 that join the tongs 56 so that the tongs 56 can be moved toward each other to fit within the side wall indentations 54 in order to grip the bucket 49 and thereby enable the bucket 49 to be transported by using the handle 50, and so that the tongs 56 can be moved away from each other to enable the handle 50 to be removed from the bucket 49 after the bucket has been transported and placed in one of the sample containment chambers 42, 44.

Figure 6:
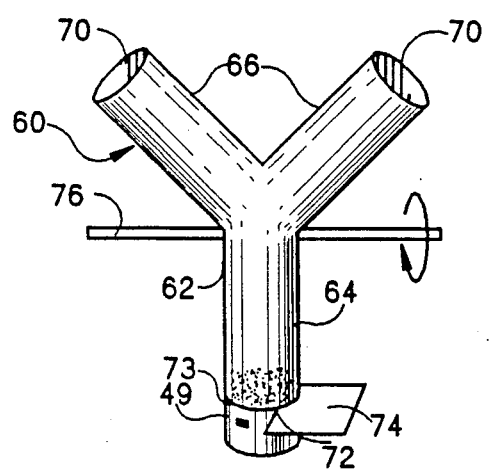
FIG. 6 is a perspective view of a sample mixer used with the bucket of FIG. 5.
Figure 4:
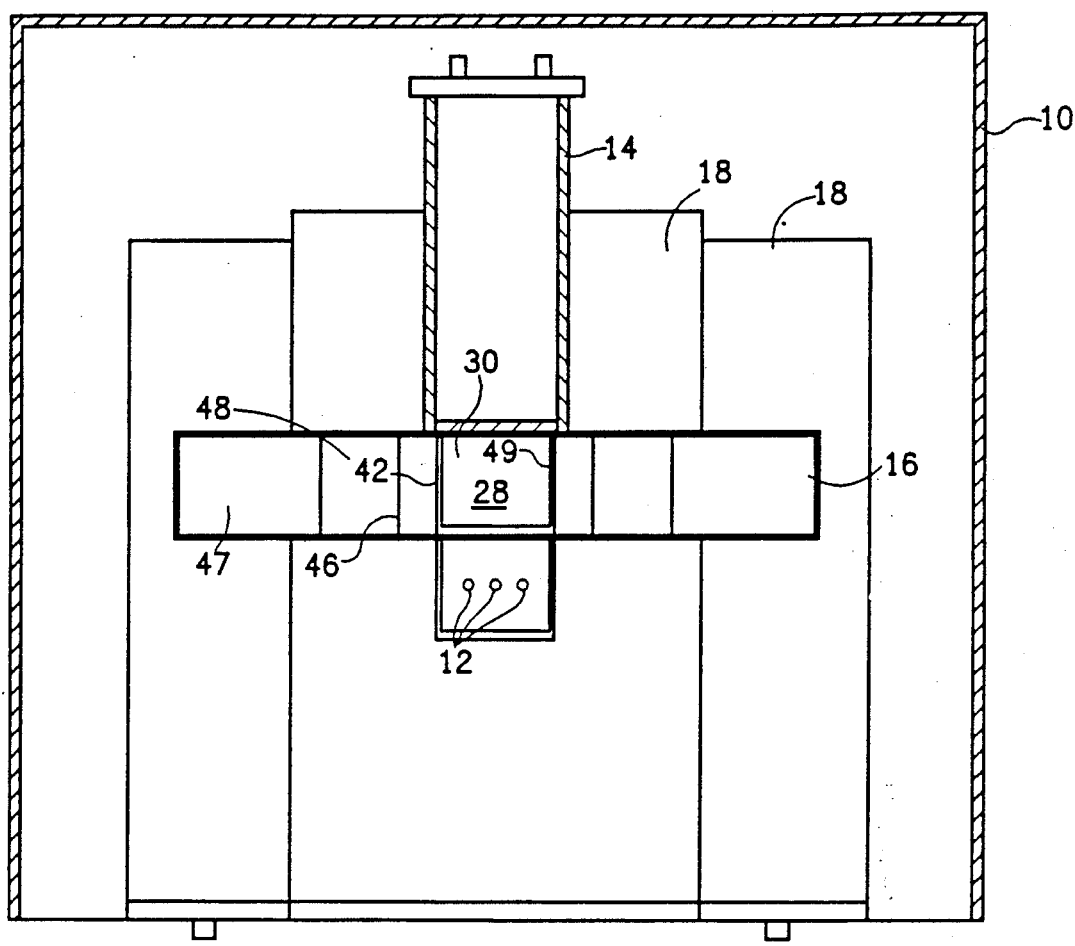
FIG. 4 is a perspective view illustrating a construction feature of the carousel.

Referring to FIG. 6, a sample mixer 60 is provided for use in throughly mixing granular material samples. The sample mixer 60 includes a Y-shaped container 62 having a hollow leg 64 and two hollow arms 66 that open into the leg 64. Each arm 66 has an extended end 70 that is closed. The leg 64 has an extended end 72 that is open and dimensioned to fit precisely against a rim 73 at the open end of the bucket 49. The open end 72 of the leg 64 thus also fits within an open end of each sample containment chamber 42, 44. In the preferred embodiment, the container 62 is made of plastic material.

A knife blade shutter 74 is attached to the extended end 72 of the leg 64 for movement between open and closed positions. When the shutter 74 is in the open position, granular material may flow into or from the container 62 through the extended end 72 of the leg 64. When the shutter 74 is in the closed position, the shutter 74 prevent granular material from flowing out of the container 62 from the extended end 72 of the leg 64.

The container 62 is disposed on an axle 76 for rotation about an axis that is normal to the leg 64 so that sample material within the container 62 can be thoroughly mixed by rotating the container 62 about the axle when the shutter 74 is in the closed position.

After a material sample 30 is thoroughly mixed by the sample mixer 60, the container is positioned over a bucket 49, with the extended end 72 of the leg 64 fitted against the rim 73 of the bucket 49; and the shutter 74 is opened to allow the sample material 30 to flow into the bucket 49. When the bucket 49 is filled to the rim 73, the knife blade shutter 74 is closed to provide a thoroughly mixed material sample that is measured to exactly fill the bucket 49 to its rim. Excess material remains in the container 62.

The present invention is also useful for analyzing material samples that are not fluid or granular, such as parcels or luggage. In an embodiment of the present invention (not shown) in which the sample containment chambers are adapted to accommodate luggage, the apparatus of the present invention may be used at airports for analyzing luggage for explosive materials.

I claim:

1. An apparatus for analyzing material samples, comprising
   a container;
   a radiation source disposed within the container;
   a detector disposed within the container for detecting radiation that is secondarily emitted by a material sample within an activation region located between the radiation source and the detector when the material sample is bombarded by radiation from the radiation source and for producing signals in response to said secondarily emitted radiation;
   a radiation shield within the container for shielding the outside of the container from radiation derived in the activation region from the radiation source;
   means for processing said signals to determine the content of the material sample; and
   means for transporting a material sample from outside the container to within said activation region;
   wherein said transporting means comprise a carousel, disposed about an axis of rotation located between the activation region and a receiving region located outside the container, and having at least one sample containment chamber that is moved between the receiving region and the activation region when the carousel is rotated about said axis.

2. An apparatus according to claim 1, wherein the carousel further includes a second sample containment chamber located on the opposite side of the carousel from the first mentioned containment chamber.

3. An apparatus according to claim 1, wherein the diameter of the carousel is greater than thirty inches, and wherein outside portions on two opposite sides of the carousel that do not contain the sample containment chamber are readily removable from a center portion of the carousel that does exceed thirty inches in width.

4. An apparatus according to claim 1, wherein the radiation source is disposed either above or below the activation region, and the detector is disposed on the opposite side of activation region from the radiation source; and
   wherein the carousel further includes a radiation shield disposed laterally around the sample containment chamber.

5. An apparatus according to claim 1, further comprising a removable bucket dimensioned for placement within the sample containment chamber, wherein the bucket includes
   a perimetric side wall having a predominant surface area that is contoured on opposite sides of the side wall to contain exterior indentations in said predominant surface area; and
   a handle, including a pair of tongs shaped and disposed for insertion into the side wall indentations, and a telescopic handle joining the tongs so that the tongs can be moved toward each other to fit within the side wall indentations in order to grip the bucket and thereby enable the bucket to be transported by using the handle, and so that the tongs can be moved away from each other to enable the handle to be removed from the bucket after the bucket has been so transported.

6. An apparatus according to claim 5, further comprising
   a sample mixer, including
   a Y-shaped container having a hollow leg and two hollow arms that open into the leg, wherein each arm has an extended end that is closed, and wherein the leg has an extended end that is open and dimensioned to fit precisely against a rim at an open end of the bucket;
   a shutter attached to the extended end of the leg for movement between open and closed positions in order to prevent sample material from flowing out of the Y-shaped container from the extended end of the leg when the shutter is in the closed position and for enabling sample material to flow into or from the Y-shaped container through the extended end of the leg when the shutter is in the open position; and
   an axle, with the Y-shaped container being disposed on the axle for rotation about an axis that is normal to the leg so that sample material within the Y-shaped container can be mixed by rotating the Y-shaped container about the axle when the shutter is in the closed position.

7. An apparatus according to claim 1, further comprising
   a sample mixer, including
   a Y-shaped container having a hollow leg and two hollow arms that open into the leg, wherein each arm has an extended end that is closed, and wherein the leg has an extended end that is open and dimensioned to fit within an open end of the sample containment chamber;

a shutter attached to the extended end of the leg for movement between open and closed positions in order to prevent sample material from flowing out of the Y-shaped container from the extended end of the leg when the shutter is in the closed position and for enabling sample material to flow into or from the Y-shaped container through the extended end of the leg when the shutter is in the open position; and an axle, with the Y-shaped container being disposed on the axle for rotation about an axis that is normal to the leg so that sample material within the Y-shaped container can be mixed by rotating the Y-shaped container about the axle when the shutter is in the closed position.

8. An apparatus according to claim 5, wherein the bucket does not extend beyond the sample containment chamber when the bucket is placed in the sample containment chamber.

9. An apparatus according to claim 8, wherein the carousel further includes a radiation shield disposed laterally around the sample containment chamber; and wherein the predominant side wall area of the bucket fits closely within the sample containment chamber when the bucket is placed in the sample containment chamber.

10. An apparatus according to claim 5, wherein the carousel further includes a radiation shield disposed laterally around the sample containment chamber; and wherein the predominant side wall area of the bucket fits closely within the sample containment chamber when the bucket is placed in the sample containment chamber.

* * * * *